United States Patent [19]

Hachmann et al.

[11] 3,948,983

[45] Apr. 6, 1976

[54] PROCESS FOR THE PREPARATION OF ACETIC ACID BY CATALYTIC GAS-PHASE OXIDATION OF BUTENES

[75] Inventors: Klaus Hachmann; Johann Gaube; Rudolf Brockhaus; Franz Langheim, all of Marl, Germany

[73] Assignee: Chemische Werke Huls Aktiengesellschaft

[22] Filed: May 21, 1974

[21] Appl. No.: 471,978

Related U.S. Application Data

[63] Continuation-in-part of Ser. No. 396,678, Sept. 13, 1973, abandoned, which is a continuation of Ser. No. 200,515, Nov. 19, 1971, abandoned.

[30] Foreign Application Priority Data

Dec. 5, 1970 Germany............................ 2059945

[52] U.S. Cl............................................. 260/533 R
[51] Int. Cl.²........................................ C07C 51/32
[58] Field of Search ................................ 260/533 R

[56] References Cited
UNITED STATES PATENTS 3,439,029   4/1969   Brockhaus...................... 260/533 R

FOREIGN PATENTS OR APPLICATIONS 990,639   4/1965   United Kingdom............. 260/533 R

*Primary Examiner*—Anton H. Sutto
*Attorney, Agent, or Firm*—Gilbert L. Wells

[57] ABSTRACT

A continuous process for the production of acetic acid by a catalytic gas-phase oxidation of butenes in the presence of a vanadate catalyst and steam and in a solid bed or fluidized bed reactor cycle is disclosed wherein the recycled gas stream contains acetic acid produced by the reaction of the butenes and oxygen or oxygen containing gases, and the butene proportion in the gaseous mixture is at least 0.4 percent by volume. A first portion of the gas stream leaving the reactor cycle is recycled and a second portion of the gas stream leaving the reactor is cooled whereby acetic acid and water are condensed. After branching the waste gas the remaining gaseous fraction of the second portion is recycled into the reactor. The volume ratio of this remaining gaseous fraction to the first portion is about 0 to 0.2 for an air feed and about 0.1 to 0.4 for an oxygen feed. The acetic acid has a concentration in the effluent gas of the reactor of about 1.5 to 10 percent by volume.

13 Claims, 1 Drawing Figure

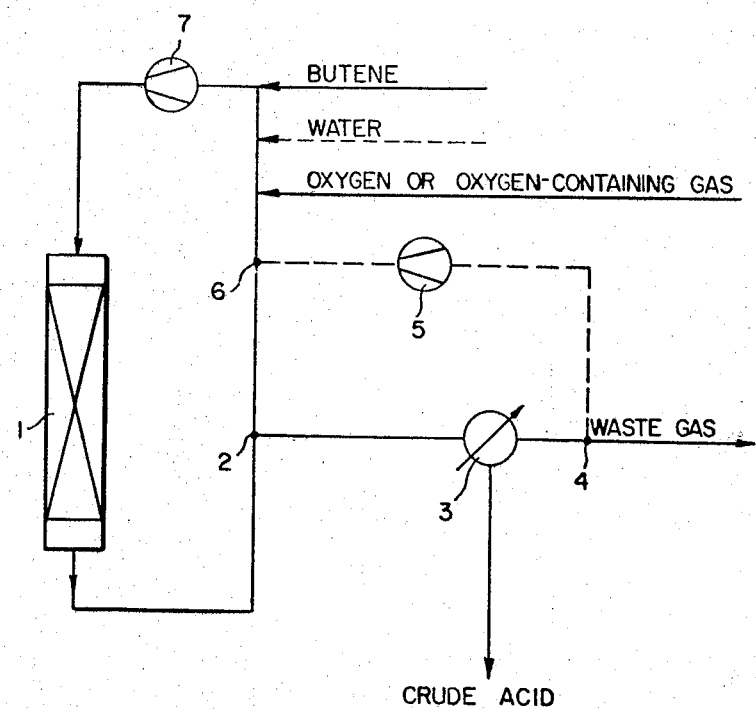

PROCESS FOR THE PREPARATION OF ACETIC ACID BY CATALYTIC GAS-PHASE OXIDATION OF BUTENES

CROSS REFERENCES TO RELATED APPLICATIONS

The present application is a Continuation-in-Part of application Ser. No. 396,678, filed Sept. 13, 1973, which in turn is a continuation of application Ser. No. 200,515, filed Nov. 19, 1971, both now abandoned.

Applicants claim priority under 35 U.S.C. 119 for Application 20 599 45, filed Dec. 5, 1970 in the Patent Office of the Federal Republic of Germany.

BACKGROUND OF THE INVENTION

The field of the invention is the preparation of carboxylic acids from hydrocarbons. The present invention is particularly concerned with a process for the preparation of acetic acid by a catalytic gas-phase oxidation of butenes.

The state of the art may be ascertained by reference to the Kirk-Othmer Encyclopedia of Chemical Technology, 2nd Ed., Vol. 8 (1966), under the section "Ethanoic Acid," pages 386–404, particularly page 396, page 397, and FIG. 5 on page 396. FIG. 5 of Kirk-Othmer discloses the process for the liquid phase oxidation of butenes to acetic acid.

The state of the prior art processes for the production of acetic acid by gas-phase oxidation of butenes in the presence of vanadate catalysts may be ascertained by reference to U.S. Pat. Nos. 3,431,297; 3,439,029; and 3,459,797, the disclosures of which are incorporated herein.

The state of the art may be further ascertained by reference to German Published Applications Nos. 1,069,150 (corresponding to British Patent No. 887,667) and 1,280,865; German Pat. Nos. 1,269,119 (corresponding to U.S. Pat. No. 3,439,029); 1,271,104 (corresponding to U.S. Pat. No. 3,459,797); and 1,279,011 (corresponding to U.S. Pat. No. 3,431,297): German unexamined published applications Nos. 1,903,190; 1,921,503; and 2,016,681, and Belgian Pat. No. 723,652.

Processes for the production of acetic acid are known from German Pat. Nos. 1,269,119 (corresponding to U.S. Pat. No. 3,439,029); 1,271,104 (corresponding to U.S. Pat. No. 3,459,797); and 1,279,011 (corresponding to U.S. Pat. No. 3,431,297), wherein butenes are reacted in the gaseous phase in the presence of a vanadate catalyst with oxygen or with oxygen-containing gases at an elevated temperature in the presence of steam. The vanadate catalysts are mixed oxides of vanadium with tin, antimony, titanium, or aluminum or vanadium metal and oxide mixtures of these metals.

In the oxidation of hydrocarbons, the final products which are thermodynamically stable are always carbon dioxide and water. The desired products, such as for example, oxides, anhydrides, or acids, are intermediate products which have only a relative stability toward a further oxidation under the reaction conditions (see inter alia, German Published Application No. 1,280,865, column 3, line 49, to column 4, line 19). For this reason, in oxidation processes of this type such as, for example, in the oxidation of ethylene to ethylene oxide or the oxidation of benzene to maleic anhydride (see German Published Application No. 1,069,150), when a cycle gas operation is used, a portion of the efflux stream leaving the reactor called cycle gas is recycled into the reactor after substantially a complete separation of the desired oxidation products.

In the production of acetic acid according to the afore-mentioned German Pat. Nos. 1,269,119 (see column 3, lines 24–28), 1,271,104 (see column 2, line 46, to column 3, line 2, as well as Example 2), and 1,279,011 (see column 3, lines 3—7), when cycle gas is used, the gaseous stream exiting from the reactor is freed of the acetic acid produced first, and then the cycle gas is branched off. In German Unexamined Published Application No. 1,921,503, which is also concerned with a process for the preparation of acetic acid by catalytic gas-phase oxidation of butenes, it is, however, disclosed that according to the state of the art a cycle gas operating method is uneconomical and therefore is no longer contemplated by those skilled in the art.

According to the prior art processes incorporated herein, the catalytic gas-phase oxidation of butene to acetic acid is conducted in the presence of steam, since it has been discovered (see German Pat. Nos. 1,269,119; 1,271,104; and 1,279,011) that the selectivity with respect to the formation of acetic acid is enhanced by steam in the reaction mixture.

When the cycle gas mode of operation is effected, according to the prior art, by separating the acetic acid from the reaction gas by condensation, water contained in the reaction gas is substantially removed. As a result, steam must be added to the reaction gas at the reactor inlet in order to maintain the steam concentration required for a sufficient selectivity for acetic acid formation in the reaction chamber. This means that, together with the acetic acid, the previously added water is obtained in the condensate along with the water formed during the side reactions resulting in CO and $CO_2$. Consequently, in this prior art mode of operation, it is possible to obtain only a moderately concentrated acetic acid with a maximum concentration of 20 percent by weight. The dehydration of the crude acid in accordance with known separating methods, such as, for example, azeotropic rectification with benzene or ethyl n-butyl ether, or liquid-liquid extraction with diisopropyl ether is, however, more expensive, the higher the water content of the crude acid. Since the above-described prior art process leads only to dilute acetic acid, the usefulness of this process on a commercial scale depends greatly on the cost of the dehydration of the acetic acid and thus on the state of the art with respect to dehydration processes.

An additional disadvantage in the above-mentioned mode of operation with cycle gas resides in that the entire gas exiting from the reactor must be cooled in a heat exchanger, to condense it, in order to separate the acetic acid substantially from the reaction gas. As a result of this required cooling to about 20° – 30°C, a large amount of the enthalpy of the gas cannot be exploited. Moreover, the use of cooling media requires considerable expense. Furthermore, a large heat exchange surface is required for cooling the entire gas, which is a considerable cost factor, especially since, in the case of acetic acid production, expensive acid-proof materials must be employed.

Attempts have been made to design the process in such a way that a more concentrated acetic acid can be obtained. In Belgian Pat. No. 723,652, a process is described wherein, by connecting several reactors in series and by feeding the butene upstream of each reactor, an acid of a higher concentration is obtained. Thus, a 31 percent by weight acid is produced in the oxidation of butene by connecting four reactors in series, but wherein after the third reactor a portion of the reaction product is condensed and withdrawn. If a higher acetic acid concentration is desired, a larger number of reactors must be connected one behind the other, which is disadvantageous for the design of a large commercial plant.

SUMMARY OF THE INVENTION

Having in mind the limitations of the prior art, it is an object of the present invention to provide a process for the catalytic gas-phase oxidation of butenes to acetic acid in a more concentrated form on a large commercial scale at an economically feasible expense.

This objective is attained, according to the invention, by providing a continuous process for the preparation of acetic acid with cycle gas operation by the catalytic gas-phase oxidation of butene and/or a mixture of butenes with oxygen or oxygen-containing gases, preferably air, in the presence of steam at an elevated temperature and optionally at an elevated pressure, in a solid bed or fluidized bed reactor. The butene proportion in the gaseous mixture in the reactor is at least 0.4 percent by volume, more advantageously at least 0.8 percent by volume and the oxidation product, acetic acid, is allowed to remain in the gaseous stream recycled into the reactor.

It was found, surprisingly, that acetic acid is stable under reaction conditions in a higher concentration, if the proportion of butenes in the reaction gas does not fall below the value of 0.4 percent by volume, more advantageously 0.8 percent by volume, at any stage of the reactor.

Accordingly, reaction conditions have been discovered which permit, contrary to the prejudice that, in gas-phase oxidations, due to the possible further oxidation of the desired oxidation product thus obtained, the latter must be separated from the cycle gas prior to returning the cycle gas into the reactor. The carrying out of a cycle gas mode of operation is advantageous for commercial and economic reasons wherein the desired product from the cycle gas is not first separated, even though, in this mode of operation, a higher concentration of the desired product, acetic acid, is produced in the reaction chamber.

Although the upper limit for the butene content is extensively arbitrary, the volume percent of butene is about 0.4 – 12, and preferably 0.8 – 6. The workable oxygen concentration in percent by volume is about 1 to 7, and preferably 2 to 4.

A limitation exists because of the explosive limits in the system butene/oxygen/inert gas, wherein the range of variation for the oxygen concentration is reduced with increasing butene content. The lower limit for the butene content is not strictly demarcated, but the drop in acetic acid yield becomes increasingly larger after passing a concentration of 0.4 percent by volume of butene in the direction of lower values.

In carrying out the continuous process, the oxygen reacted with the butenes may be introduced as pure oxygen diluted with an inert gas such as nitrogen, e.g., air. The gas stream leaving the reactor is divided into a first portion to be recycled and a second portion which is cooled, whereby acetic acid and water are condensed.

After branching the waste gas, the remaining gaseous fraction is recycled into the reactor. In the case of a pure oxygen feed the volume ratio of this remaining gaseous fraction to the first portion is about 0.1 – 0.4, while in the base of an air feed, the volume ratio is about 0 to 0.2.

Usually the acetic acid concentration in the effluent gas of the reactor is in percent by volume about 1.5 to 10, and preferably 2 to 5. Naturally, the reaction must be carried out under such conditions that no condensation of acetic acid and water occurs in the reaction.

BRIEF DESCRIPTION OF THE DRAWING

The FIGURE of the drawing shows the flow sheet of the process in simplified form.

The fresh gas components butene or butenes, oxygen, or oxygen-containing gas, and optionally water or steam, are added to the gaseous stream after the junction point 6. The reactor 1 can be a solid bed reactor or a fluidized bed reactory. The gaseous stream exiting from the reactor 1 is divided at branching point 2. A partial stream is fed to a separating unit 3, generally a condenser, wherein the acetic acid and the water are extensively separated and are obtained as aqueous crude acid. The entire gaseous stream exiting from the separating unit 3 is withdrawn as waste gas, if no gas is conducted from the branching point 4 to the junction point 6. Unreacted butene can be separated from the waste gas stream and returned to the reactor.

The stream of crude acid leaving the separating unit 3 is fed to a separating plant to remove water and readily volatile oxidation products, such as acetaldehyde and acetone. The easily volatile oxidation products are suitably recycled into the reactor. Of the water thus separated, the amount corresponding to the formation of water of reaction is branched off as waste water and the remainder can be fed to the reaction system as inlet water.

The gaseous stream coming from the branching point 2 is fed, together with the fresh gas, to the cycle gas compressor 7 bringing the gaseous mixture, prior to entrance into the reactor, to the pressure level ambient upstream of the reactor. The gaseous stream exiting from the separating unit 3 can be divided, at the branching point 4, into a waste gas stream and into a gaseous stream conducted to the compressor 5. The gaseous stream passing the compressor 5 is then combined at the junction point 6 with the gaseous stream coming from the branching point 2.

In the process of this invention, the ratio of the gaseous streams combined at 6 and constituting the cycle gas is an essential process variable. When conducting the process with air, no gas is suitably conducted from 4 to 6, i.e. the cycle gas has the same composition as the gaseous stream exiting from the reactor.

In case pure oxygen is employed, the waste gas stream is very minor, due to the missing nitrogen proportion, so that, without the feeding of gas from 4 to 6, the concentrations of acetic acid and water in the reaction chamber would be elevated to such an extent that condensation would occur. The catalyst would then be destroyed. Therefore, when conducting the process with oxygen, the gaseous stream conducted through the separating unit 3 should be increased. This is effected by conducting gas from the branching point 4 to the junction point 6.

The ratio of the volumes of the streams from the branching point 4 to the junction point 6 and from the branching point 2 to the junction point 6 are preferably, when operating with air, in the range of 0 to 0.2, preferably 0; and when operating with oxygen, in the range of 0.1 – 0.4, preferably 0.2.

The ratio of the volumes of the streams when using any desired oxygen-containing gases can be determined by linear interpolation or extrapolation of the aforementioned range data.

DESCRIPTION OF THE PREFERRED EMBODIMENTS

As suitable starting materials for the process, butenes are used, such as cis- and trans-butene-2, n-butene-1, and isobutene, and/or mixtures of butenes. All n-butenes result in the same acetic acid yield. When using isobutene, the yield in acetic acid (amount of acetic acid to the amount of reacted butene) is normally lower than in the use of n-butenes. It is also possible to employ $C_4$-hydrocarbon mixtures containing butane, for example $C_4$-cuts produced in the ethylene/propylene preparation in steam cracking plants, and from which butadiene and optionally isobutene were separated.

As the oxidizing agent, oxygen or an oxygen-containing gas, predominantly air, is used.

As mentioned above, a concentration of steam in the reaction gas has a favorable effect on the selectivity with respect to the formation of acetic acid.

In the process of the present invention, due to the special cycle gas circulation, steam is always present at the reactor inlet as a result of side reactions, without having to supply additional steam to the process. Thereby, it is possible to obtain a crude acid having an acetic acid proportion of about 60–65 percent by weight. If steam is fed to the process, the yield in acetic acid is increased, but an acid of a lower concentration is obtained. Whether, and how much, steam is to be supplied to the process depends on economical considerations. However, in general, no more steam should be supplied in the process of this invention than required for producing a 30 percent by weight acid.

The molar ratios of the initial substances fed to the process, namely butene or butenes, oxidizing agent, and steam, can be varied, considering the flammability limits of the resultant mixture. In general, the starting materials are used in molar ratios which can range, for butene/oxygen, from 0.1–0.6, and for steam/butene, from 0–6.

The catalytic gas-phase oxidation of butene to acetic acid can be conducted in all types of reactors suitable for the gas-phase oxidation, such as solid bed or fluidized bed reactors.

Catalysts which can be employed in this connection are all catalysts suitable for the acetic acid production by gas-phase oxidation of butenes. Heretofore, catalysts proved advantageous for this oxidation consisting of mixed oxides wherein one component is vanadium, (German Unexamined Published Applications Nos. 1,903,190 and 1,921,503).

Catalysts of mixed oxides of vanadium with tin, antimony, titanium, or aluminum, or of vanadium with oxide mixtures of these metals, which can be optionally present on an inert substrate, preferably silicic acid, are preferably employed (see German Pat. Nos. 1,269,119; 1,271,104; 1,279,011; as well as German Unexamined Published Application No. 2,016,681).

The average residence time of the gaseous mixture in the catalyst chamber can be varied within certain limits; however, this period should be about 1 second to 10 seconds in the case of the solid bed reactor, and about 2 seconds to 20 seconds in the case of the fluidized bed reactor.

The temperature used during the gas-phase oxidation is dependent respectively on the catalyst employed and can comprise a temperature range of approximately 160°C to about 400°C. Preferably, the process is operated at temperatures of 170° – 250°C.

Suitably, the reaction is conducted at higher pressures, about 10 – 40 atmospheres absolute for the solid bed and 1.5 – 15 atmospheres absolute for the fluidized bed, since the work to be expended for the circulation of the cycle gas decreases with increasing pressure. In contrast thereto, when air is used as the oxidating agent, the amount of work expended for compression of the fresh air is increased. The minimum of the sum of work required for the cycle gas circulation and the air compression is within the above-mentioned pressure ranges.

At comparable reaction temperatures and gas compositions, the space-time yield increases with increasing pressure. Furthermore, the amount of work required for separating the aqueous crude acid from the gaseous mixture by condensation is likewise smaller when using higher pressures.

In connection with the solid bed reactor, it has proved to be advantageous to operate at medium pressures of between 15 and 30 atmospheres absolute. In the case of the fluidized bed reactor, pressures of 2 – 5 atmospheres absolute are preferably employed.

According to the present invention, the prior art formulations of cycle gas processes wherein the entire reactor discharge gas is conducted through a condenser, as well as the disadvantages wherein a series of reactors are connected one behind the other and wherein butene is fed in front of each reactor, are eliminated, without observing a reduction in yield. Thus, for example, 1.30 kg of acetic acid per kg. of reacted butene is obtained in the process of this invention, when a 35 percent by weight acetic acid is produced (Table, Experiment No. 6). In the process with cycle gas operation, wherein the entire reactor discharge gas is subjected to condensation, 1.33 kg. of acetic acid is produced per kg. of reacted butene, to produce a 20 percent by weight acetic acid (see the Table, Comparative Experiment No. 7). Practically an identical yield of 1.35 kg. of acetic acid per kg. of reacted butene is attained in the process using series-connected reactors and intermediate feeding of butene, when a 30 percent by weight acetic acid is produced (see Belgian Pat. No. 723,652).

A special advantage of the process of the present invention resides in its flexibility with respect to the attainable concentration of the crude acetic acid produced in this manner. The process can be operated in such a way that an aqueous crude acid of up to about 65 percent by weight is obtained without the requirement of a complicated and expensive mode of operation for the process. However, the aforementioned flexibility makes it possible, above all, to adapt the process to the respective economical conditions determined predominantly by the processes for acid dehydration and the time-dependent relationship of the cost factors of raw material and energy. Independently of the fact whether a more dilute or a more concentrated acid is produced, when using the process of the present invention, the expenses for separating the crude acid by means of condensation from the gaseous stream are reduced to a fraction of the conventionally required costs. An additional advantage of the process is afforded in that the heat losses are very minor, and almost the entire heat produced in the reactor can be exploited, for example, for the production of heating steam.

densation, i.e. practically no acetic acid is recycled into the reactor.

In the catalyst column Ti/V means titanium vanadate and Sn/V means tin vanadate. The designation S in Column 3 means oxygen and A is air. $Nm^3/h$ in columns 3, 5 and 6 means cubic meters per hour at normal conditions of temperature and pressure.

TABLE

| Catalyst | Ti/V | | | | | | | | Sn/V | Ti/V iso-Butene |
|---|---|---|---|---|---|---|---|---|---|---|
| Hydrocarbon | n-Butene | | | | | | | | | |

| Column | 1 | 2 | 3 | 4 | 5 | 6 | 7 | 8 | 9 | | 10 | 11 |
|---|---|---|---|---|---|---|---|---|---|---|---|---|
| Experiment No. | T (°C) | Butene Feed (kg/h) | Air or Oxygen Feed ($Nm^3/h$) | Steam Feed (kg/h) | Partial Stream 2→6 ($Nm^3/h$) | Partial Stream 4→6 ($Nm^3/h$) | Butene Conversion (%) | kg Acetic Acid per kg Reacted Butene | Concentration of Crude Acid | | Butene Conc. Reactor Outlet (% by Vol.) | Pressure (atm. abs.) |
| | | | | | | | | | Acetic Acid (% by Wt.) | Formic Acid (% by Wt.) | | |
| 1 | 185 | 0.367 | S 0.57 | 0 | 10.1 | 3.9 | 91 | 0.98 | 53 | 7 | 3.4 | 21 |
| 2 | 185 | 0.367 | S 0.54 | 0.18 | 10.1 | 3.7 | 90 | 1.14 | 46 | 5 | 3.9 | 21 |
| 3 | 185 | 0.367 | S 0.51 | 0.54 | 10.1 | 3.3 | 90 | 1.27 | 35 | 3 | 4.0 | 21 |
| 4 | 185 | 0.395 | A 2.32 | 0 | 12.3 | — | 66 | 0.98 | 56 | 7 | 2.3 | 21 |
| 5 | 185 | 0.395 | A 2.14 | 0.18 | 12.2 | — | 64 | 1.15 | 45 | 4 | 2.7 | 21 |
| 6 | 185 | 0.395 | A 2.07 | 0.46 | 11.8 | — | 63 | 1.30 | 35 | 2 | 2.8 | 21 |
| 7 | 185 | 0.452 | A 2.59 | 2.01 | — | 15.0 | 93 | 1.33 | 20 | 0.5 | 0.5 | 21 |
| 8 | 200 | 0.525 | A 3.12 | — | 12.4 | — | 74 | 0.98 | 56 | 6 | 1.7 | 21 |
| 9 | 200 | 0.250 | A 2.01 | — | 12.5 | — | 92 | 0.75 | 46 | 5 | 0.4 | 21 |
| 10 | 185 | 0.435 | A 1.79 | — | 12.2 | — | 63 | 0.96 | 54 | 7 | 3.6 | 10 |
| 11 | 210 | 0.315 | A 1.52 | — | 12.5 | — | 58 | 0.92 | 55 | 33 | 3.5 | 21 |
| 12 | 180 | 0.450 | A 2.92 | — | 12.8 | — | 70 | 0.58 | 38 | 4 | 1.8 | 21 |

S: Oxygen
A: Air

EXAMPLES (See in this connection the Table and FIG. 1)

A conventional solid bed reactor, consisting of a steel pipe, was filled with 3.8 liters of a titanium vanadate catalyst. The reactor was charged with the amount of butene set forth in column 2 of the Table, the amount of air or oxygen set forth in column 3, and the amount of steam set forth in column 4. The streams of matter branched off upstream of the condensation (partial stream 2 → 6) and downstream of the condensation (partial stream 4 → 6) are disclosed in column 5 and column 6. In the Table, the respective butene conversion is listed (column 7); also, the Table indicates the quantity of acetic acid produced, based on the respective amount of converted butene (column 8) and the composition of the crude acid thus obtained (column 9). In columns 1, 10 and 11, the temperature, the butene concentration at the reactor outlet, as well as the pressure in the reactor are set forth, respectively.

The oxygen concentration at the reactor outlet was always 3 percent by volume. The readily volatile oxidation products, such as for example, acetaldehyde and acetone, were recycled into the reactor.

Examples 1, 2, and 3 demonstrate the feasability of producing crude acid of varying concentration for a mode of operation with the use of oxygen, whereas Examples, 4, 5, and 6 demonstrate this possibility in connection with a mode of operation with the use of air.

The values set forth in Example 7 are meant for comparison. In this experiment, the entire gas exiting from the reactor is subjected, as conventional, to a condensation, and the cycle gas is branched off after the con-

We claim:

1. In a process for the production of acetic acid by the catalytic gas phase oxidation of butenes in a reactor cycle having a vanadate catalyst, the improvement comprising carrying out the process continuously by reacting about 0.4 to 12 percent by volume of butenes with about 1 to 7 percent by volume of oxygen at a temperature of about 160° – 400°C in the presence of steam to produce a gas stream leaving the reactor containing acetic acid produced by the reaction of said butenes and said oxygen and recycling a portion of said acetic acid containing gas stream, said acetic acid having a concentration in the effluent gas of the reactor of about 1.5 to 10 percent by volume.

2. The process of claim 1, wherein said volume of butene is about 0.8 to 6 percent and said volume of oxygen is about 2 to 4 percent.

3. The process of claim 1, wherein said acetic acid concentration is about 2 to 5 percent by volume.

4. The process of claim 1, wherein the reactor cycle has a solid bed reactor and the pressure is about 10 – 40 atmospheres absolute.

5. The process of claim 1, wherein the reactor cycle has a fluidized bed reactor and the pressure is about 1.5 – 15 atmospheres absolute.

6. The process of claim 1, wherein said oxygen is introduced as an air feed, a first portion of the gas stream leaving the reactor is recycled, a second portion of the gas stream leaving the reactor is cooled, whereby acetic acid and water are condensed and after branching the waste gas the remaining gaseous fraction of the second portion is recycled into the reactor, the volume ratio of this remaining gaseous fraction to the first portion is about 0 to 0.2.

7. The process of claim 1, wherein said oxygen is introduced as an oxygen feed, a first portion of the gas stream leaving the reactor is recycled and a second portion of the gas stream leaving the reactor is cooled, whereby acetic acid and water are condensed and after branching the waste gas the remaining gaseous fraction of the second portion is recycled into the reactor, the volume ratio of this remaining gaseous fraction to the first portion is about 0.1 – 0.4.

8. The process of claim 6, wherein the volume ratio of the remaining gaseous fraction of the second portion to the first portion is 0.

9. The process of claim 7, wherein the volume ratio of the remaining gaseous fraction of the second portion to the first portion is 0.2.

10. The process of claim 4, wherein the pressure is about 15 – 30 atmospheres absolute.

11. The process of claim 5, wherein the pressure is about 2 – 5 atmospheres absolute.

12. The process of claim 1, wherein the temperature is 170° – 250°C.

13. The process of claim 1, wherein an acetic acid proportion of about 60 – 65 percent by weight is obtained as a crude acid product.

* * * * *